United States Patent [19]
Ulrich et al.

[11] Patent Number: 6,121,274
[45] Date of Patent: Sep. 19, 2000

[54] DIHYDROBENZOFURANE

[75] Inventors: Wolf-Rüdiger Ulrich; Ulrich Thibaut, both of Constance, Germany

[73] Assignee: Byk Gulden Lomberg Chemische Fabrik GmbH, Constance, Germany

[21] Appl. No.: 08/750,920

[22] PCT Filed: Jul. 19, 1995

[86] PCT No.: PCT/EP95/02841

§ 371 Date: Apr. 15, 1997

§ 102(e) Date: Apr. 15, 1997

[87] PCT Pub. No.: WO96/03399

PCT Pub. Date: Feb. 8, 1996

[30] Foreign Application Priority Data

Jul. 22, 1994 [CH] Switzerland .......................... 02323/94

[51] Int. Cl.[7] ...................... A61K 31/438; A61K 31/343; C07D 405/04; C07D 405/06

[52] U.S. Cl. .......................... 514/278; 546/15; 546/282.7; 546/284.1; 549/331; 549/343; 549/345; 549/469; 549/471; 514/337; 514/450; 514/451; 514/456; 514/461; 514/462

[58] Field of Search .................................... 546/15, 282.7, 546/284.1; 549/471, 469, 331, 343, 345; 514/278, 337, 456, 450, 451, 461, 462

[56] References Cited

U.S. PATENT DOCUMENTS 5,340,827   8/1994   Beeley et al. ........................... 514/352

*Primary Examiner*—Alan L. Rotman
*Attorney, Agent, or Firm*—Jacobson, Price, Holman & Stern, PLLC

[57] ABSTRACT

The invention concerns componuds of formula (I), in which R1, R2, R3 and R4 have the meanings given in the description. The compounds are novel, effective PDE-inhibitors.

12 Claims, No Drawings

DIHYDROBENZOFURANE

FIELD OF APPLICATION OF THE INVENTION

The invention relates to novel compounds which are used in the pharmaceutical industry for the production of medicaments.

KNOWN TECHNICAL BACKGROUND

International Patent Application WO92/12961 describes benzamides having PDE-inhibiting properties.—International Patent Application WO93/25517 discloses trisubstituted phenyl derivatives as selective PDE-IV inhibitors.—International Patent Application WO94/02465 describes inhibitors of c-AMP phosphodiesterase and of TNF.

DESCRIPTION OF THE INVENTION

It has been found that the benzamides described in greater detail below, which differ from the previously published compounds by completely different substitution in positions 2 and 3 on the benzamide, have surprising and particularly advantageous properties.

The invention thus relates to compounds of the formula I (see attached formula sheet I) in which R1 is 1–6C-alkoxy, 3–7C-cycloalkoxy, 3–7C-cycloalkylmethoxy, benzyloxy or completely or partially fluorine-substituted 1–4C-alkoxy, R2 is 1–4C-alkyl and R3 is hydrogen or 1–4C-alkyl, or R2 and R3, together and including the two carbon atoms to which they are bonded, are a 5-, 6- or 7-membered hydrocarbon ring, if desired interrupted by an oxygen atom, R4 is phenyl, pyridyl, R41-, R42- and R43-substituted phenyl or R44-, R45-, R46- and R47-substituted pyridyl, where R41 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino, R42 is hydrogen, hydroxyl, halogen, amino, trifluoromethyl, 1–4C-alkyl or 1–4C-alkoxy, R43 is hydrogen, halogen, 1–4C-alkyl or 1–4C-alkoxy, R44 is hydroxyl, halogen, cyano, carboxyl, 1–4C-alkyl, 1–4C-alkoxy, 1–4C-alkoxycarbonyl or amino, R45 is hydrogen, halogen, amino or 1–4C-alkyl, R46 is hydrogen or halogen and R47 is hydrogen or halogen, the salts of these compounds, and the N-oxides of the pyridines and their salts.

1–6C-alkoxy is a radical which, beside the oxygen atom, contains a straight-chain or branched alkyl radical having 1 to 6 carbon atoms. Alkyl radicals having 1 to 6 carbon atoms which may be mentioned here are, for example, the hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-cycloalkoxy is, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-cycloalkylmethoxy is, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Completely or partially fluorine-substituted 1–4C-alkoxy radicals which may be mentioned are, for example, the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and the difluoromethoxy radicals.

5-, 6- or 7-membered hydrocarbon rings, if desired interrupted by an oxygen atom, which may be mentioned are the cyclopentane, the cyclohexane, the cycloheptane, the tetrahydrofuran and the tetrahydropyran rings. If R2 and R3, together and including the two carbon atoms to which they are bonded, form a 5-, 6- or 7-membered ring, a spiro compound is present.

1–4C-alkyl is straight-chain or branched alkyl radicals having 1 to 4 carbon atoms. Examples which may be mentioned are the butyl, isobutyl, sec-butyl, tert-butyl, propyl, isopropyl, ethyl and methyl radicals.

Halogen within the meaning of the present invention is bromine, chlorine or fluorine.

1–4C-alkoxy is a radical which, beside the oxygen atom, contains one of the abovementioned 1–4C-alkyl radicals. Examples which may be mentioned are the methoxy and the ethoxy radicals.

1–4C-alkoxycarbonyl is a carbonyl group to which one of the abovementioned 1–4C-alkoxy radicals is bonded. Examples which may be mentioned are the methoxycarbonyl ($CH_3O$—CO—) and the ethoxycarbonyl radicals ($CH_3CH_2O$—CO).

1–4C-alkylcarbonyl is a carbonyl group to which one of the abovementioned 1–4C-alkyl radicals is bonded. An example which may be mentioned is the acetyl radical ($CH_3CO$—).

1–4C-alkylcarbonyloxy radicals contain, beside the oxygen atom, one of the abovementioned 1–4C-alkylcarbonyl radicals. An example which may be mentioned is the acetoxy radical ($CH_3CO$—O—).

Mono- or di-1–4C-alkylamino radicals which may be mentioned are, for example, the methylamino, the dimethylamino and the diethylamino radicals.

A 1–4C-alkylcarbonylamino radical which may be mentioned is, for example, the acetylamido radical (NH—CO—$CH_3$).

Exemplary, R41-, R42- and R43-substituted phenyl radicals which may be mentioned are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6 fluorophenyl, 2-hydroxyphenyl, 2-hydroxy-4-methoxyphenyl, 2,4-dihydroxyphenyl, 2-methoxyphenyl, 2,3-dimethoxyphenyl, 2,4-dimethoxyphenyl, 2,6-dimethoxyphenyl, 2-dimethylaminophenyl, 2-methylphenyl, 2-chloro-6-methylphenyl, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl and 2,6-dichloro-4-ethoxycarbonylphenyl.

Exemplary, R44-, R45-, R46- and R47-substituted pyridyl radicals which may be mentioned are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid-2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromopyrid-2-yl, 3,5-dibromopyrid-4-yl, 3,5-dichloropyrid-4-yl, 2,6-dichloropyrid-3-yl, 3,5-dimethylpyrid-4-yl, 3-chloro-2,5,6-trifluoropyrid-4-yl and 2,3,5-trifluoropyrid-4-yl.

Suitable salts of compounds of the formula I—depending on substitution—are all acid addition salts, but in particular all salts with bases. Particular mention may be made of the pharmacologically tolerable salts of the inorganic and organic acids and bases customarily used in pharmacy. Pharmacologically nontolerable salts which, for example, are initially formed as process products during the preparation of the compounds according to the invention on the industrial scale, are converted into pharmacologically tolerable salts by processes known to the person skilled in the art. Those which are suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible for the acids to be employed in salt preparation—depending on whether it is a mono- or polybasic acid and depending on what salt is required—in an equimolar quantitative ratio or one differing therefrom.

On the other hand, salts with bases are also especially suitable. Examples of basic salts which may be mentioned are lithium, sodium, potassium, calcium, aluminum, magnesium, titanium, ammonium, meglumine or guanidinium salts, here too the bases being employed during salt preparation in an equimolar quantitative ratio or one differing therefrom.

Compounds of the formula I to be emphasized are those in which

R1 is 1–4C-alkoxy, 3–5C-cycloalkoxy, 3–5C-cycloalkylmethoxy, or completely or partially fluorine-substituted 1–4C-alkoxy, R2 is 1–4C-alkyl and R3 is hydrogen or 1–4C-alkyl, or R2 and R3, together and including the two carbon atoms to which they are bonded, are a cyclopentane, cyclohexane, tetrahydrofuran or tetrahydropyran ring, R4 is phenyl, pyridyl, R41-, R42- and R43-substituted phenyl or R44-, R45-, R46- and R47-substituted pyridyl, where R41 is halogen, cyano, carboxyl, 1–4C-alkyl, 1–4C-alkoxy, or 1–4C-alkoxycarbonyl, R42 is hydrogen, halogen, 1–4C-alkyl or 1–4C-alkoxy, R43 is hydrogen, halogen, 1–4C-alkyl or 1–4C-alkoxy, R44 is halogen or 1–4C-alkyl, R45 is hydrogen or halogen, R46 is hydrogen or halogen and R47 is hydrogen or halogen, the salts of these compounds, and the N-oxides of the pyridines and their salts.

Compounds of the formula I particularly to be emphasized are those in which

R1 is 1–4C-alkoxy, 3–5C-cycloalkoxy, 3–5C-cycloalkylmethoxy, or completely or partially fluorine-substituted 1–4C-alkoxy, R2 is 1–4C-alkyl and R3 is hydrogen or 1–4C-alkyl, or R2 and R3, together and including the two carbon atoms to which they are bonded, are a cyclopentane, cyclohexane, tetrahydrofuran or tetrahydropyran ring, R4 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 3,5-difluropyrid-4-yl, 2-chlorophenyl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, the salts of these compounds, and the N-oxides of the pyridines and their salts.

Preferred compounds of the formula I are those in which

R1 is methoxy, ethoxy, cyclopropylmethoxy, difluoromethoxy, trifluoromethoxy or 2,2,2-trifluoroethoxy, R2 is methyl or ethyl and R3 is hydrogen or methyl, or R2 and R3, together and including the two carbon atoms to which they are bonded, are a cyclopentane, cyclohexane, tetrahydrofuran or tetrahydropyran ring, R4 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 3,5-difluoropyrid-4-yl, 2-chlorophenyl, 2,3,5,6-tetrafluoropyrid-4-yl, 3-chloro-2,5,6-trifluoropyrid4-yl, 3,5-dichloro-2,6-difluoropyrid-4-yl or 2,6-dichloropyrid-3-yl, the salts of these compounds, and the N-oxides of the pyridines and their salts.

Particularly preferred compounds of the formula I are those in which

R1 is methoxy, ethoxy, cyclopropylmethoxy, difluoromethoxy, trifluoromethoxy or 2,2,2-trifluoroethoxy, R2 is methyl or ethyl and R3 is hydrogen or methyl, or R2 and R3, together and including the two carbon atoms to which they are bonded, are a cyclopentane, cyclohexane, tetrahydrofuran or tetrahydropyran ring, R4 is 3,5-dichloropyrid-4-yl, 2,6-dichlorophenyl or 2,6-difluorophenyl, the salts of these compounds, and the N-oxides of the pyridines and their salts.

Exemplary compounds according to the invention are listed in the following tables:

TABLE 1

Compounds of the formula I (see attached formula sheet I) with R4 = 3,5-dichloropyrid-4-yl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | $CH_2CH_2CH_2$ | |
| $OC_2H_5$ | $CH_2CH_2CH_2$ | |
| $OCH_2C_3H_5$ | $CH_2CH_2CH_2$ | |
| $OCF_2H$ | $CH_2CH_2CH_2$ | |
| $OCF_3$ | $CH_2CH_2CH_2$ | |
| $OCH_2CF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCH_2C_3H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_2CF_3$ | $CH_2CH_2CH_2CH_2$ | |
| $OCH_3$ | $CH_2$—O—$CH_2$ | |
| $OC_2H_5$ | $CH_2$—O—$CH_2$ | |
| $OCH_2C_3H_5$ | $CH_2$—O—$CH_2$ | |
| $OCF_2H$ | $CH_2$—O—$CH_2$ | |
| $OCF_3$ | $CH_2$—O—$CH_2$ | |
| $OCH_2CF_3$ | $CH_2$—O—$CH_2$ | |
| $OCH_3$ | $CH_2CH_2$—O | |
| $OC_2H_5$ | $CH_2CH_2$—O | |
| $OCH_2C_3H_5$ | $CH_2CH_2$—O | |
| $OCF_2H$ | $CH_2CH_2$—O | |
| $OCF_3$ | $CH_2CH_2$—O | |
| $OCH_2CF_3$ | $CH_2CH_2$—O | |
| $OCH_3$ | $CH_2CH_2$—O—$CH_2$ | |
| $OC_2H_5$ | $CH_2CH_2$—O—$CH_2$ | |
| $OCH_2C_3H_5$ | $CH_2CH_2$—O—$CH_2$ | |
| $OCF_2H$ | $CH_2CH_2$—O—$CH_2$ | |
| $OCF_3$ | $CH_2CH_2$—O—$CH_2$ | |
| $OCH_2CF_3$ | $CH_2CH_2$—O—$CH_2$ | |

TABLE 2

Compounds of the formula I (see attached formula sheet I) with R4 = 2,6-dichlorophenyl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | $CH_2CH_2CH_2$ | |
| $OC_2H_5$ | $CH_2CH_2CH_2$ | |
| $OCH_2C_3H_5$ | $CH_2CH_2CH_2$ | |
| $OCF_2H$ | $CH_2CH_2CH_2$ | |
| $OCF_3$ | $CH_2CH_2CH_2$ | |
| $OCH_2CF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCH_2C_3H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_2CF_3$ | $CH_2CH_2CH_2CH_2$ | |
| $OCH_3$ | $CH_2$—O—$CH_2$ | |
| $OC_2H_5$ | $CH_2$—O—$CH_2$ | |
| $OCH_2C_3H_5$ | $CH_2$—O—$CH_2$ | |
| $OCF_2H$ | $CH_2$—O—$CH_2$ | |
| $OCF_3$ | $CH_2$—O—$CH_2$ | |
| $OCH_2CF_3$ | $CH_2$—O—$CH_2$ | |
| $OCH_3$ | $CH_2CH_2$—O | |
| $OC_2H_5$ | $CH_2CH_2$—O | |
| $OCH_2C_3H_5$ | $CH_2CH_2$—O | |
| $OCF_2H$ | $CH_2CH_2$—O | |
| $OCF_3$ | $CH_2CH_2$—O | |
| $OCH_2CF_3$ | $CH_2CH_2$—O | |
| $OCH_3$ | $CH_2CH_2$—O—$CH_2$ | |
| $OC_2H_5$ | $CH_2CH_2$—O—$CH_2$ | |
| $OCH_2C_3H_5$ | $CH_2CH_2$—O—$CH_2$ | |
| $OCF_2H$ | $CH_2CH_2$—O—$CH_2$ | |
| $OCF_3$ | $CH_2CH_2$—O—$CH_2$ | |
| $OCH_2CF_3$ | $CH_2CH_2$—O—$CH_2$ | |

TABLE 3

Compounds of the formula I (see attached formula sheet I) with R4 = 2,6-difluorophenyl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | $CH_2CH_2CH_2$ | |
| $OC_2H_5$ | $CH_2CH_2CH_2$ | |
| $OCH_2C_3H_5$ | $CH_2CH_2CH_2$ | |
| $OCF_2H$ | $CH_2CH_2CH_2$ | |
| $OCF_3$ | $CH_2CH_2CH_2$ | |
| $OCH_2CF_3$ | $CH_2CH_2CH_2$ | |
| $OCH_3$ | $CH_2CH_2CH_2CH_2$ | |
| $OC_2H_5$ | $CH_2CH_2CH_2CH_2$ | |
| $OCH_2C_3H_5$ | $CH_2CH_2CH_2CH_2$ | |
| $OCF_2H$ | $CH_2CH_2CH_2CH_2$ | |
| $OCF_3$ | $CH_2CH_2CH_2CH_2$ | |
| $OCH_2CF_3$ | $CH_2CH_2CH_2CH_2$ | |
| $OCH_3$ | $CH_2$—O—$CH_2$ | |
| $OC_2H_5$ | $CH_2$—O—$CH_2$ | |
| $OCH_2C_3H_5$ | $CH_2$—O—$CH_2$ | |
| $OCF_2H$ | $CH_2$—O—$CH_2$ | |
| $OCF_3$ | $CH_2$—O—$CH_2$ | |
| $OCH_2CF_3$ | $CH_2$—O—$CH_2$ | |
| $OCH_3$ | $CH_2CH_2$—O | |
| $OC_2H_5$ | $CH_2CH_2$—O | |
| $OCH_2C_3H_5$ | $CH_2CH_2$—O | |
| $OCF_2H$ | $CH_2CH_2$—O | |
| $OCF_3$ | $CH_2CH_2$—O | |
| $OCH_2CF_3$ | $CH_2CH_2$—O | |
| $OCH_3$ | $CH_2CH_2$—O—$CH_2$ | |
| $OC_2H_5$ | $CH_2CH_2$—O—$CH_2$ | |

TABLE 3-continued

Compounds of the formula I (see attached formula sheet I) with R4 = 2,6-difluorophenyl and the following further substituents meanings:

| R1 | R2 | R3 |
|---|---|---|
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 4

Compounds of the formula I (see attached formula sheet I) with R4 = 2-chloropyrid-3-yl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 5

Compounds of the formula I (see attached formula sheet I) with R4 = 2-chloro-6-methylphenyl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 6

Compounds of the formula I (see attached formula sheet I) with R4 = 2-chloro-6-fluorophenyl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |

TABLE 6-continued

Compounds of the formula I (see attached formula sheet I) with R4 = 2-chloro-6-fluorophenyl and the following further substituents meanings:

| R1 | R2 | R3 |
|---|---|---|
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ |

TABLE 7

Compounds of the formula I (see attached formula sheet I) with R4 = 3,5-difluoropyrid-4-yl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |

TABLE 7-continued

Compounds of the formula I (see attached formula sheet I) with R4 = 3,5-difluoropyrid-4-yl and the following further substituents meanings:

| R1 | R2 | R3 |
|---|---|---|
| $OCF_3$ | | $CH_2CH_2$—O—$CH_2$ |
| $OCH_2CF_3$ | | $CH_2CH_2$—O—$CH_2$ |

TABLE 8

Compounds of the formula I (see attached formula sheet I) with R4 = 2-chlorophenyl and the following further substituents meanings:

| R1 | R2 | R3 |
|---|---|---|
| $OCH_3$ | $CH_3$ | H |
| $OC_2H_5$ | $CH_3$ | H |
| $OCH_2C_3H_5$ | $CH_3$ | H |
| $OCF_2H$ | $CH_3$ | H |
| $OCF_3$ | $CH_3$ | H |
| $OCH_2CF_3$ | $CH_3$ | H |
| $OCH_3$ | $C_2H_5$ | $CH_3$ |
| $OC_2H_5$ | $C_2H_5$ | $CH_3$ |
| $OCH_2C_3H_5$ | $C_2H_5$ | $CH_3$ |
| $OCF_2H$ | $C_2H_5$ | $CH_3$ |
| $OCF_3$ | $C_2H_5$ | $CH_3$ |
| $OCH_2CF_3$ | $C_2H_5$ | $CH_3$ |
| $OCH_3$ | | $CH_2CH_2CH_2$ |
| $OCF_3$ | | $CH_2CH_2CH_2$ |
| $OCH_2CF_3$ | | $CH_2CH_2CH_2$ |
| $OCH_3$ | | $CH_2CH_2CH_2CH_2$ |
| $OC_2H_5$ | | $CH_2CH_2CH_2CH_2$ |
| $OCH_2C_3H_5$ | | $CH_2CH_2CH_2CH_2$ |
| $OCF_2H$ | | $CH_2CH_2CH_2CH_2$ |
| $OC_2H_5$ | | $CH_2CH_2CH_2$ |
| $OCH_2C_3H_5$ | | $CH_2CH_2CH_2$ |
| $OCF_2H$ | | $CH_2CH_2CH_2$ |
| $OCF_3$ | | $CH_2CH_2CH_2CH_2$ |
| $OCH_2CF_3$ | | $CH_2CH_2CH_2CH_2$ |
| $OCH_3$ | | $CH_2$—O—$CH_2$ |
| $OC_2H_5$ | | $CH_2$—O—$CH_2$ |
| $OCH_2C_3H_5$ | | $CH_2$—O—$CH_2$ |
| $OCF_2H$ | | $CH_2$—O—$CH_2$ |
| $OCF_3$ | | $CH_2$—O—$CH_2$ |
| $OCH_2CF_3$ | | $CH_2$—O—$CH_2$ |
| $OCH_3$ | | $CH_2CH_2$—O |
| $OC_2H_5$ | | $CH_2CH_2$—O |
| $OCH_2C_3H_5$ | | $CH_2CH_2$—O |
| $OCF_2H$ | | $CH_2CH_2$—O |
| $OCF_3$ | | $CH_2CH_2$—O |
| $OCH_2CF_3$ | | $CH_2CH_2$—O |
| $OCH_3$ | | $CH_2CH_2$—O—$CH_2$ |
| $OC_2H_5$ | | $CH_2CH_2$—O—$CH_2$ |
| $OCH_2C_3H_5$ | | $CH_2CH_2$—O—$CH_2$ |
| $OCF_2H$ | | $CH_2CH_2$—O—$CH_2$ |
| $OCF_3$ | | $CH_2CH_2$—O—$CH_2$ |
| $OCH_2CF_3$ | | $CH_2CH_2$—O—$CH_2$ | and the salts of the compounds mentioned in the tables.

The compounds of the formula I are chiral compounds if the substituents —R2 and —CH₂R3 are not identical. The invention therefore comprises both the pure enantiomers and their mixtures in any mixing ratio, including the racemates.

The invention further relates to a process for the preparation of the compounds of the formula I and their salts, and also the N-oxides of the pyridines and their salts. The process comprises reacting compounds of the formula II (see attached formula sheet I), in which R1, R2 and R3 have the meanings indicated above and X is a suitable leaving group, with amines R4—NH₂, and, if desired, then converting compounds of the formula I obtained into their salts and/or converting pyridines obtained into the N-oxides and, if desired, then into the salts, or, if desired, then converting salts of the compounds of the formula I obtained into the free compounds.

The person skilled in the art is familiar on the basis of his expert knowledge with suitable leaving groups X. For example, starting materials are suitable acid halides of the formula II (X=Cl or Br). Otherwise, the reaction is carried out, for example, as described in the following examples, or in a manner familiar per se to the person skilled in the art (e.g. as described in the International Patent Application WO 92/12961).

The N-oxidation is carried out in a manner which is also familiar to the person skilled in the art, e.g. with the aid of m-chloroperoxybenzoic acid in dichloromethane at room temperature. The person skilled in the art is familiar on the basis of his expert knowledge with the reaction conditions which are specifically necessary for carrying out the process.

The isolation and purification of the substances according to the invention is carried out in a manner known per se, for example by distilling off the solvent in vacuo and recrystallizing the residue obtained from a suitable solvent or subjecting it to one of the customary purification methods, such as, for example, column chromatography on a suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol), which contains the desired acid or base, or to which the desired acid or base is then added. The salts are obtained by filtering, reprecipitating, precipitating with a nonsolvent for the addition salt or by evaporating the solvent. Salts obtained can be converted by basification or by acidification into the free compounds which, in turn, can be converted into salts. In this manner, pharmacologically nontolerable salts can be converted into pharmacologically tolerable salts.

The compounds of the formula II can be prepared according to the general reaction scheme on the attached formula sheet II. By way of example, the preparation of compounds of the formula II is described in the following examples under "starting compounds". The preparation of further compounds of the formula II can be carried out in an analogous manner.

The amines R4—NH$_2$ are known, or they can be prepared in a known manner.

The following examples illustrate the invention in greater detail, without restricting it.

The abbreviation RT stands for room temperature, h stands for hour(s), min for minute(s) and m.p. for melting point.

EXAMPLES

Final Products 1. 2,3-Dihydro-2,2-dimethyl-7-methoxybenzofuran-4-carboxylic acid-N-3,5-dichloro-4-pyridylamide 0.22 g of sodium hydride (80% in paraffin) is suspended in 20 ml of anhydrous THF and a solution of 0.5 g of 4-amino-3,5-dichloropyridine in 5 ml of abs. THF is then added dropwise with stirring. The mixture is stirred for 30 min and a solution of 2,3-dihydro-2,2-dimethyl-7-methoxybenzofuran-4-carbonyl chloride (prepared from 0.8 g of 2,3-dihydro-2,2-dimethyl-7-methoxybenzofuran-4-carboxylic acid, see example A1) in 10 ml of abs. THF is then added dropwise. After 10 min, it is poured onto water, adjusted to pH 4 with 2N HCl, extracted 3 times with ethyl acetate, and the combined extracts are dried over sodium sulfate and filtered. The oily residue which remains after concentrating in a rotary evaporator is chromatographed on a silica gel column using dichloromethane/methanol (98:2). The chromatographically pure fractions are combined, concentrated and crystallized using diethyl ether. 0.7 g of the title compound of m.p. 140–142° C. is obtained.

2. 2,3-Dihydro-7-methoxybenzofuran-2-spiro-1'-cyclopentan-4-carboxylic acid-N-3,5-dichloro-4-pyridylamide Analogously to Example 1, 0.55 g of sodium hydride (80% in paraffin) in 50 ml of abs. THF, 1.5 g of 4-amino-3,5-dichloropyridine in 20 ml of abs. THF and 2.5 g of 2,3-dihydro-7-methoxybenzofuran-2-spiro-1'-cyclopentane-4-carbonyl chloride give 1.4 g of the title compound of m.p. 168–170° C. (from diethyl ether).

3. 7-Difluoromethoxy-2,3-dihydrobenzofuran-2-spiro-1'-cyclopentane-4-carboxylic acid-N-3,5-dichloro-4-pyridylamide Analogously to Example 1, 0.15 g of sodium hydride (80% in paraffin) in 20 ml of abs. THF, 0.41 g of 4-amino-3,5-dichloropyridine in 10 ml of abs. THF and a solution of 7-difluoromethoxy-2,3-dihydrobenzofuran-2-spiro-1'-cyclopentane-4-carbonyl chloride (prepared from 0.7 g of 7-difluoromethoxy-2,3-dihydrobenzofuran-2-spiro-1'-cyclopentane-4-carboxylic acid, see Example C1) in 10 ml of abs. THF give, after chromatography (silica gel, eluent: ethyl acetate/petroleum ether 4:6), 0.15 g of the title compound of m.p. 152–153° C. (from diisopropyl ether).

4. 2,3-dihydro-7-methoxybenzofuran-2-spiro-1'-cyclohexane-4-carboxylic acid-N-3,5-dichloro-4-pyridylamide Analogously to Example 1, 0.46 g of sodium hydride (80% in paraffin) in 20 ml of abs. THF, 1.24 g of 4-amino-3,5-dichloropyridine in 20 ml of abs. THF and a solution of 2,3-dihydro-7-methoxybenzofuran-2-spiro-1'-cyclohexane-4-carbonyl chloride (prepared from 2 g of 2,3-dihydro-7-methoxybenzofuran-2-spiro-1'-cyclohexane-4-carboxylic acid, see Example D1) in 20 ml of abs. THF give 2.9 g of the title compound of m.p.: 169–170° C.

5. 2,3-Dihydro-7-methoxybenzofuran-2-spiro-1'-(4'-oxacyclohexane)-4-carboxylic acid-N-3,5-dichloro-4-pyridylamide Analogously to Example 1, 0.22 g of sodium hydride in 40 ml of abs. THF, 0.62 g of 4-amino-3,5-dichloropyridine in 20 ml of abs. THF and a solution of 2,3-dihydro-7-methoxybenzofuran-2-spiro-1'-(4'-oxacyclohexane)-4-carbonyl chloride (prepared from 1 g of 2,3-dihydro-7-methoxybenzofuran-2-spiro-1'-(4'-oxacyclohexane)-4-carboxylic acid, see Example E1) in 10 ml of abs. THF give 0.3 g of the title compound of m.p.: 208–210° C.

6. 2,2-Diethyl-2,3-dihydro-7-methoxybenzofuran-4-carboxylic acid-N-3,5-dichloro-4-pyridylamide Analogously to Example 1, 0.3 g of sodium hydride (80% in paraffin) in 20 ml of abs. THF, 0.8 g of 4-amino-3,5-dichloropyridine in 10 ml of abs. THF and a solution of 2,2-diethyl-2,3-dihydro-7-methoxybenzofurancarbonyl chloride (prepared from 1.2 g of 2,2-diethyl-2,3-dihydro-7-methoxybenzofuran-4-carboxylic acid, see Example F1) in 20 ml of THF give, after chromatography (silica gel, dichloromethane, methanol 98:2), 0.9 g of the title compound of m.p.: 171–172° C.

7. 2,3-Dihydro-7-methoxybenzofuran-2-spiro-1'-cyclopentane-4-carboxylic acid-2,6-dichloroanilide A solution of 0.65 g of 2,6-dichloroaniline and 0.7 ml of triethylamine in 20 ml of dioxane is warmed to 40–50° C. and a solution of 2,3-dihydro-7-methoxybenzofuran-2-spiro-1'-cyclopentane-4-carbonyl chloride (prepared from 1 g of 2,3-dihydro-7-methoxybenzofuran-2-spiro-1'-cyclopentane-4-carboxylic acid, see Example A1) in 10 ml of dioxane is then added dropwise. The mixture is stirred at 50° C. for 1 h, then it is poured onto water and extracted with ethyl acetate. The organic extract is dried over sodium sulfate and concentrated, and the residue is chromatographed on a silica gel column using ethyl acetate/petroleum ether 4:6. The chromatographically pure fractions are combined, concentrated and crystallized using diisopropyl ether. 0.2 g of the title compound of m.p.: 172–174° C. is obtained.

8. 2,3-Dihydro-7-methoxybenzofuran-2-spiro-1'-cyclopentane-4-carboxylic acid-2,6-difluoroanilide Analogously to Example 7, 0.65 ml of 2,6-difluoroaniline, 0.9 ml of triethylamine and 2,3-dihydro-7-methoxybenzofuran-2-spiro-1'-cyclopentane-4-carbonyl chloride (prepared from 1.5 g of carboxylic acid, see Example A1) give 1.2 g of the title compound of m.p.: 142–145° C. (from diisopropyl ether).

Starting Compounds

A1: 2,3-Dihydro-2,2-dimethyl-7-methoxybenzofuran-4-carbonyl chloride 0.8 g of 2,3-dihydro-2,2-dimethyl-7-methoxybenzofuran-4-carboxylic acid is heated to boiling under reflux for 1 h in a mixture of 50 ml of abs. toluene and 3 ml of thionyl chloride. The solvent is distilled off in a rotary evaporator and toluene (about 30 ml) is then added a further 2 times and the mixture is concentrated again. The residue is dried in a high vacuum and employed in Example 1 without further purification.

A2: 2,3-Dihydro-2,2-dimethyl-7-methoxybenzofuran-4-carboxylic acid 5.5 g of methyl 2,3-dihydro-2,2-dimethyl-7-methoxybenzofuran-4-carboxylate are stirred at 60° C. for 2 h in a mixture of 150 ml of ethanol and 50 ml of 2N NaOH. The ethanol is distilled off, the residue is taken up in the water and the solution is adjusted to a pH of 4 with 2N HCl. The product which is precipitated hereby is filtered off with suction, washed with water and dried. 4.7 g of the title compound of m.p. 147–149° C. are obtained.

A3: Methyl 1 2,3-dihydro-2,2-dimethyl-7-methoxybenzofuran-4-carboxylate 15.6 g of methyl 3-hydroxy-4-methoxy-2-(2-methyl-2-propenyl)benzoate are dissolved in 250 ml of abs. dichloromethane and the solution is treated with 3 ml of concentrated sulfuric acid. The mixture is stirred at RT for 12 h, then it is treated with water and a pH of 5 is set in the aqueous phase by addition of 2N NaOH. After separating off the organic phase, the aqueous phase is extracted a further 2 times with ethyl acetate. The combined organic phases are concentrated and the oily residue is chromatographed on a silica gel column using ethyl acetate/petroleum ether (4:6). The chromatographically pure fractions of the product with $R_f$=0.6 are combined and concentrated. 6.6 g of the title compound of m.p. 65–67° C. are obtained.

A4: Methyl-3-hydroxy-4-methoxy-2-(2-methyl-2-propenyl)-benzoate 20 g of methyl 4-methoxy-3-(2-methyl-2-propenyloxy) benzoate are dissolved in 60 ml of quinoline and the mixture is heated at 180–190° C. for 2 h. After cooling, it is treated with ethyl acetate and the quinoline is extracted using 2N HCl. The organic phase is washed a further 2 times with water and concentrated. The oily residue is chromatographed on a silica gel column using ethyl acetate/petroleum ether (4:6). The chromatographically pure fractions are combined, concentrated and dried in a high vacuum. 15.6 g of the title compound are obtained as a pale yellow oil.

A5: Methyl 4-methoxy-3-(2-methyl-2-propenyloxy) benzoate 22 g of methyl 3-hydroxy-4-methoxybenzoate are dissolved in 200 ml of anhydrous DMF and 41 g of ground potassium carbonate and 14.7 ml of 3-chloro-2-methylpropene are then added. The mixture is stirred at 60° C. for 5 h. After cooling, the precipitate is filtered off with suction, water is added to the filtrate and it is then extracted 3 times with ethyl acetate. The residue which remains after concentrating the extracts is crystallized using petroleum ether. 21 g of the title compound of m.p. 62–63° C. are obtained.

B1: 2,3-Dihydro-7-methoxybenzofuran-2-spiro-1'-cyclopentane-4-carbonyl chloride The title compound is prepared analogously to starting compound A1 from 2,3-dihydro-7-methoxybenzofuran-2-spiro-1'-cyclopentane-4-carboxylic acid in 50 ml of abs. toluene and 3 ml of thionyl chloride and reacted further without further purification.

B2: 2,3-dihydro-7-methoxybenzofuran-2-spiro-1'-cyclopentane-4-carboxylic acid 2.6 g of methyl 2,3-dihydro-7-methoxybenzofuran-2-spiro-1'-cyclopentane-4-carboxylate are hydrolyzed analogously to Example A2 in 50 ml of ethanol and 10 ml of 2N NaOH. 2.3 g of the title compound of m.p. 166–168° C. are obtained.

B3: Methyl 2,3-dihydro-7-methoxybenzofuran-2-spiro-1'-cyclopentane-4-carboxylate 10.2 g of methyl 2-cyclopenten-1-ylmethyl-3-hydroxy-4-methoxybenzoate are dissolved in 500 ml of anhydrous n-hexane and treated with about 5 g of Amberlyst 15. The mixture is stirred at RT for 3 days, filtered and concentrated. The residue is chromatographed on a silica gel column using ethyl acetate/petroleum ether (4:6), the chromatographically pure fractions are combined and concentrated and the residue is dried in a high vacuum. 7.2 g of the title compound are obtained as a yellow oil.

B4: Methyl 2-cyclopenten-1-ylmethyl-3-hydroxy-4-methoxybenzoate 12.7 g of methyl 3-(2-methylenecyclopentyloxy)-4-methoxybenzoate are treated with 50 ml of quinoline and the mixture is stirred at 190° C. for 1 h. After cooling, it is treated with water, adjusted to pH 3 using 2N HCl and extracted with ethyl acetate. The residue which remains after concentrating the solvent is chromatographed on a silica gel column using ethyl acetate/petroleum ether (4:6). The chromatographically pure fractions are concentrated and dried in a high vacuum. 10.2 g of the title compound are obtained as a yellow oil.

B5: methyl 3-(2-methylenecyclopentyloxy)-4-methoxybenzoate 28.5 g of methyltriphenylphosphonium bromide are suspended under nitrogen in 300 ml of anhydrous THF and the mixture is cooled to −40° C. 50 ml of n-butyllithium (1.6M) in n-hexane are then added dropwise with stirring. After stirring at −20° to −10° for 30 min, a solution of 20 g of methyl 4-methoxy-3-(2-oxocyclopentyloxy)benzoate in 100 ml of abs. THF is added dropwise. The mixture is then allowed to warm to RT and is stirred for a further 1 h. It is poured onto water and extracted with ethyl acetate. The oil which remains after concentrating the organic phase is chromatographed on a silica gel column using ethyl acetate/petroleum ether (4:6). The chromatographically pure fractions are combined, concentrated and dried in a high vacuum. 12.7 g of the title compound are obtained as a colorless oil.

B6: Methyl 4-methoxy-3-(2-oxocyclopentyloxy) benzoate 23.8 g of methyl 3-hydroxy-4-methoxybenzoate are dissolved in 200 ml of anhydrous DMF and the solution is treated with 35 g of potassium carbonate (ground) and 13 ml of 2-chlorocyclopentanone. The mixture is stirred at 60° C. for 3 h, then the solid is filtered off with suction and the filtrate is concentrated in vacuo. The residue is chromatographed on a silica gel column using ethyl acetate/petroleum ether (4:6). The chromatographically pure fractions are combined, concentrated and dried in a high vacuum. 24.3 g of the title compound are obtained as a pale yellow oil.

C1: 7-Difluoromethoxy-2,3-dihydrobenzofuran-2-spiro-1'-cyclopentane-4-carbonyl chloride Analogously to Example A1, 0.7 g of 7-difluoromethoxy-2,3-dihydrobenzofuran-2-spiro-1'-cyclopentane-4-carboxylic acid are reacted in a mixture of 20 ml of abs. toluene and 2 ml of thionyl chloride and used in the next step without further purification.

C2: 7-Difluoromethoxy-2,3-dihydrobenzofuran-2-spiro-1'-cyclopentane-4-carboxylic acid Analogously to Example A2, 2.4 g of ethyl 7-difluoromethoxy-2,3-dihydrobenzofuran-2-spiro-1'-cyclopentane-4-carboxylate gives 2 g of the title compound of m.p.: 143–145° C.

C3: Ethyl 7-difluoromethoxy-2,3-dihydrobenzofuran-2-spiro-1'-cyclopentane-4-carboxylate 2.7 g of ethyl 2,3-dihydro-7-hydroxybenzofuran-2-spiro-1'-cyclopentane-4-carboxylate are dissolved in 70 ml of dioxane, 3 ml of 50% NaOH solution and 0.1 g of benzyltrimethylammonium chloride are added and then difluorochloromethane is passed into the mixture with stirring at 70–75° C. until the reaction has ended (about 1 h). After cooling, the mixture is poured onto water and extracted 3 times with 100 ml of ethyl acetate. After drying over sodium sulfate, the organic phase is concentrated and the residue is chromatographed on a silica gel column using ethyl acetate/petroleum ether 4:6. The chromatographically pure fractions are combined, concentrated and dried in a high vacuum. 2.4 g of the title compound are obtained as a pale yellow oil.

C4: Ethyl 2,3-dihydro-7-hydroxybenzofuran-2-spiro-1'-cyclopentane-4-carboxylate 4.1 g of ethyl 7-benzyloxy-2,3-dihydrobenzofuran-2-spiro-1'-cyclopentane-4-carboxylate, 0.5 g of Pd/C (10%) and 20 ml of cyclohexane are heated to boiling under reflux for 4 h in 100 ml of toluene. After cooling, the mixture is filtered and the filtrate is concentrated to dryness. 2.7 g of the title compound are obtained as a pale brown oil.

C5: Ethyl 7-benzyloxy-2,3-dihydrobenzofuran-2-spiro-1'-cyclopentane-4-carboxylate 10 g of methyltriphenylphosphonium bromide-sodium amide mixture (FLUKA 69500) are suspended in 100 ml of abs. THF under an $N_2$ atmosphere and stirred at RT for 0.5 h. A solution of 7 g of ethyl 4-benzyloxy-3-(2-oxocyclopentyloxy)benzoate in 20 ml of abs. THF is then added dropwise in the course of 30 min. The mixture is stirred at RT for 2 h, then it is poured onto water and extracted 3 times with 100 ml of ethyl acetate. After drying over sodium sulfate, the organic phase is concentrated to dryness. For rearrangement, the oily residue is stirred at 190° C. for 1.5 h. After cooling, 100 ml of toluene and 10 g of Amberlyst 15 (anhydrous) are added and the mixture is stirred at 80° C. for 3 h. It is then filtered and washed with methanol, and the filtrate is concentrated to dryness. The residue is chromatographed on a silica gel column using ethyl acetate/petroleum ether 4:6. The fractions containing the main product ($R_f$~0.8) are combined, concentrated and dried in a high vacuum. 4.1 g of the title compound are obtained as a pale yellow oil.

C6: Ethyl 4-benzyloxy-3-(2-oxocyclopentyloxy) benzoate

Analogously to Example B6, 34 g of ethyl 4-benzyloxy-3-hydroxybenzoate, 35 g of potassium carbonate and 15 ml of 2-chlorocyclopentanone give 36 g of the title compound as a colorless oil.

D1: 2,3-Dihydro-7-methoxybenzofuran-2-spiro-1'-cyclohexane-4-carbonyl chloride Analogously to Example A1, 2 g of 2,3-dihydro-7-methoxybenzofuran-2-spiro-1'-cyclohexane-4-carboxylic acid are reacted with 5 ml of thionyl chloride in 50 ml of toluene.

D2: 2,3-Dihydro-7-methoxybenzofuran-2-spiro-1'-cyclohexane-4-carboxylic acid Analogously to Example A1, 10.3 g of methyl 2,3-dihydro-7-methoxybenzofuran-2-spiro-1'-cyclohexane-4-carboxylate give 9 g of the title compound of m.p.: 171–173° C.

D3: Methyl 2,3-dihydro-7-methoxybenzofuran-2-spiro-1'-cyclohexane-4-carboxylate Analogously to Example B3, 17 g of methyl 2-cyclohexen-1-ylmethyl-3-hydroxy-4-methoxybenzoate in 500 ml of n-hexane and 15 g of Amberlyst 15 (4 h at 60° C.) give 10.3 g of the title compound as a yellow oil.

D4: Methyl 2-cyclohexen-1-ylmethyl-3-hydroxy-4-methoxy-benzoate

Analogously to Example B4, 21 g of methyl 3-(2-methylenecyclohexyloxy)-4-methoxybenzoate (reaction 2 h at 190° C.) give 17 g of the title compound as a yellow oil.

D5: Methyl 3-(2-methylenecyclohexyloxy)-4-methoxy-benzoate 43.8 g of methyltriphenylphosphonium bromide in 300 ml of abs. dimethoxyethane are treated in portions under nitrogen with 3.6 g of sodium hydride (80% in paraffin). The mixture is stirred at RT for 1 h and a solution of 30 g of methyl 4-methoxy-3-(2-oxocyclohexyloxy)benzoate is then slowly added dropwise. The mixture is stirred at RT overnight and then worked up analogously to Example B5. 21 g of the title compound are obtained as a colorless oil.

D6: Methyl 4-methoxy-3-(2-oxocyclohexyloxy) benzoate

Analogously to Example B6, 25 g of methyl 3-hydroxy-4-methoxybenzoate, 41 g of potassium carbonate and 17.5 ml of 2-chlorocyclohexanone in 200 ml of DMF give 32.9 g of the title compound as a pale yellow oil.

E1: 2,3-Dihydro-7-methoxybenzofuran-2-spiro-1'-(4'-oxacyclohexane)-4-carbonyl chloride Analogously to Example A1, 1 g of 2,3-dihydro-7-methoxybenzofuran-2-spiro-1'-(4'-oxacyclohexane)-4-carboxylic acid are reacted in a mixture of 50 ml of toluene and 5 ml of thionyl chloride and further processed without further purification.

E2: 2,3-Dihydro-7-methoxybenzofuran-2-spiro-1'-(4'-oxacyclohexane)-4-carboxylic acid Analogously to Example A2, 1.3 g of methyl 2,3-dihydro-7-methoxybenzofuran-2-spiro-1'-(4'-oxacyclohexane)-4-carboxylate are hydrolyzed in a mixture of 50 ml of methanol and 10 ml of 1N sodium hydroxide solution. 1 g of the title compound of m.p.: 194–196° C. is obtained.

E3: Methyl 2,3-dihydro-7-methoxybenzofuran-2-spiro-1'-(4'-oxacyclohexane)-4-carboxylate 3.6 g of methyl 4-methoxy-3-(4-methylenetetrahydropyran-3-yloxy)benzoate are dissolved in 50 ml of quinoline and the solution is stirred at 190–200° C. for 1 h. After cooling, it is poured onto water, and the mixture is adjusted to pH 3 using 2 N hydrochloric acid and extracted 3 times with ethyl acetate. After drying over sodium sulfate, the organic phase is concentrated to dryness in vacuo and the residue (2.9 g) is dissolved in 150 ml of n-hexane. The solution is treated with 2.9 g of Amberlyst 15 and vigorously stirred at 60° C. for 4 h. It is then filtered, the filtrate is concentrated in vacuo and the oily residue is chromatographed on a silica gel column using ethyl acetate/petroleum ether 4:6. The chromatographically pure fractions are combined, concentrated and dried in a high vacuum. 1.3 g of the title compound are obtained as a pale yellow oil.

E4: Methyl 4-methoxy-3-(4-methylenetetrahydropyran-3-yloxy)benzoate 18.2 g of methyltriphenylphosphonium bromide are suspended in 200 ml of dimethoxyethane under a nitrogen atmosphere and 1.5 g of sodium hydride (80% in paraffin) are then added in portions. The mixture is stirred at RT for 3 h and a solution of 13 g of methyl 4-methoxy-3-(4-oxotetrahydropyran-3-yloxy)benzoate are then added dropwise in the course of 30 min. The mixture is stirred overnight, then poured onto water and extracted 3 times with ethyl acetate. After drying over sodium sulfate, the organic phase is concentrated in vacuo and the residue is chromatographed on a silica gel column using ethyl acetate/petroleum ether 4:6. The chromatographically pure fractions are combined, concentrated and dried in a high vacuum. 3.6 g of the title compound are obtained as a pale yellow oil.

E5: Methyl 4-methoxy-3-(4-oxotetrahydropyran-3-yloxy)benzoate

Analogously to Example B6, 36.4 g of methyl 3-hydroxy-4-methoxybenzoate, 50 g of potassium carbonate and 27 g of 3-chlorotetrahydropyran-4-one in 200 ml of DMF give 11.5 g of the title compound as a pale yellow oil.

F1: 2,2-Diethyl-2,3-dihydro-7-methoxybenzofuran-4-carbonyl chloride

Analogously to Example A1, 1.2 g of 2,2-diethyl-2,3-dihydro-7-methoxybenzofuran-4-carboxylic acid are reacted in a mixture of 10 ml of toluene and 2 ml of thionyl chloride.

F2: 2,2-Diethyl-2,3-dihydro-7-methoxybenzofuran-4-carboxylic acid 1.5 g of methyl 2,2-diethyl-2,3-dihydro-7-methoxybenzofuran-7-carboxylate are hydrolyzed in a mixture of 20 ml of ethanol and 5 ml of 2N sodium hydroxide solution analogously to Example A2 and worked up. 1.2 g of the title compound of m.p.: 152–154° C. are obtained.

F3: Methyl 2,2-diethyl-2,3-dihydro-7-methoxybenzofuran-4-carboxylate 10 of methyltriphenylphosphonium bromide-sodium amide mixture (FLUKA 69500) are added to 100 ml of abs. THF at about 10° C. under protective gas (nitrogen), and the mixture is warmed to RT and stirred for about 30 min. A solution of 5.3 g of methyl 4-methoxy-3-(1-methyl-2-oxobutoxy)benzoate is then added dropwise. The mixture is stirred at RT for 1 h, then poured onto water and extracted 3 times with about 50 ml of ethyl acetate. The combined extracts are dried over sodium sulfate and concentrated, and the oily residue is dried in a high vacuum. The oil obtained (3.8 g) is stirred at 190–200° C. for 1 h, cooled and dissolved in 100 ml of toluene. The solution is treated with 5 g of Amberlyst 15 and vigorously stirred at 80° C. overnight. The Amberlyst is then filtered off, the solution is concentrated and the residue is chromatographed on a silica gel column using ethyl acetate/petroleum ether 4:6. The chromatographically pure fractions are combined and concentrated, and the residue is dried in a high vacuum. 1.5 g of the title compound are obtained as a pale yellow oil.

F4: Methyl 4-methoxy-3-(1-methyl-2-oxobutoxy) benzoate

Analogously to Example B6, 48.5 g of methyl 3-hydroxy-4-methoxybenzoate, 83 g of potassium carbonate and 43.9 g of 2-bromopentan-3-one in 200 ml of DMF give 68 g of the title compound of m.p.: 63–65° C. (stirring with petroleum ether).

Commercial Utility

The compounds according to the invention have useful pharmacological properties which make them commercially utilizable. As cyclic nucleotide phosphodiesterase (PDE) inhibitors (to be precise of type IV), they are suitable on the one hand as bronchial therapeutics (for the treatment of airway obstructions on account of their dilating but also on account of their respiratory rate- and respiratory drive-increasing action), but on the other hand especially for the treatment of disorders, in particular of inflammatory nature, e.g. of the airways (asthma prophylaxis), of the skin, of the intestine, of the eyes and of the joints, which are mediated by mediators such as histamine, PAF (platelet-activating factor), arachidonic acid derivatives such as leukotrienes and prostaglandins, cytokines, interleukins IL-1 to IL-12, alpha-, beta- and gamma-interferons, tumor necrosis factor (TNF) or oxygen free radicals and proteases. The compounds according to the invention are distinguished here by a low toxicity, a good enteral absorption (high bioavailability), a wide therapeutic range and the absence of significant side effects.

On account of their PDE-inhibiting properties, the compounds according to the invention can be employed in human and veterinary medicine as therapeutics, it being possible to use them, for example, for the treatment and prophylaxis of the following diseases: acute and chronic (in particular inflammatory and allergen-induced) airway disorders of varying genesis (bronchitis, allergic bronchitis, bronchial asthma); dermatoses (especially of proliferative, inflammatory and allergic nature) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritic type (rheumatoid arthritis, rheumatoid spondylitis, osteoarthritis and other arthritic conditions), disorders of the immune system (AIDS), types of shock [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and the adjacent regions (paranasal sinuses, eyes), such as allergic rhinitis/sinusitis, chronic rhinitis sinusitis, allergic conjunctivitis and also nasal polyps; but also disorders of the heart which can be treated by PDE inhibitors, such as, for example, cardiac insufficiency, or disorders which can be treated on account of the tissue-relaxing action of the PDE inhibitors, such as colics of the kidneys and of the ureters in connection with kidney stones; or alternatively disorders of the CNS, such as, for example, depression or arteriosclerotic dementia.

The invention further relates to a method for the treatment of mammals, including humans, which are suffering from one of the abovementioned diseases. The method comprises administering to the sick mammal a therapeutically active and pharmacologically tolerable amount of one or more of the compounds according to the invention.

The invention further relates to the compounds according to the invention for use in the treatment and/or propylaxis of the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned, which contain one or more of the compounds according to the invention.

The medicaments are prepared by processes known per se which are familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on account of his expert knowledge with the auxiliaries which are suitable for the desired pharmaceutical formulations. Beside solvents, gel-forming agents, ointment bases and other active compound excipients, for example, antioxidants, dispersants, emulsifiers, preservatives, solubilizers or permeation promoters can be used.

For the treatment of disorders of the respiratory tracts the compounds according to the invention are preferably also administered by inhalation. To this end, these are either administered directly as powders (preferably in micronized form) or by atomizing solutions or suspensions which contain them. With respect to the preparations and administration forms, reference is made, for example, to the details in European Patent 163 965.

For the treatment of dermatoses, the administration of the compounds according to the invention takes place, in particular, in the form of those medicaments which are suitable for topical application. For the production of the medicaments, the compounds according to the invention (=active compounds) are preferably mixed with suitable pharmaceutical auxiliaries and processed further to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds is carried out in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 0.5 mg/kg. The customary dose in the case of systemic therapy is between 0.05 and 2 mg/kg per day.

Biological Investigations

In the investigation of PDE IV inhibition at the cellular level, the activation of inflammatory cells is ascribed particular importance. An example which may be mentioned is the FMLP (N-formyl-methionyl-leucyl-phenylalanine)-induced superoxide production of neutrophilic granulocytes, which can be measured as luminol-potentiated chemoluminescence. (Mc Phail L C, Strum S L, Leone P A and Sozzani S, The neutrophil respiratory burst mechanism. In "Immunology Series" 57: 47–76, 1992; ed. Coffey R G (Marcel Decker, Inc., New York-Basle-Hong Kong)).

Substances which inhibit the chemoluminescence and the cytokine secretion and the secretion of proinflammatory mediators of inflammatory cells, in particular neutrophilic and eosinophilic granulocytes, are those which inhibit PDE IV. This isoenzyme of the phosphodiesterase families is particularly represented in granulocytes. Its inhibition leads to the raising of the intracellular cyclic AMP concentration and thus to the inhibition of cellular activation. PDE IV inhibition by the substances according to the invention is thus a central indicator of the suppression of inflammatory processes (Giembycz M A, Could isoenzyme-selective phosphodiesterase inhibitors render bronchodilatory therapy redundant in the treatment of bronchial asthma?. Biochem Pharmacol 43: 2041–2051, 1992; Torphy T J et al., Phosphodiesterase inhibitors; new opportunities for treatment of asthma. Thorax 46: 512–523, 1991; Schudt C et al., Zardaverine: a cyclic AMP PDE III/IV inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and $Ca_i$. Naunyn-Schmiedebergs Arch Pharmacol 344: 682–690, 1991; Nielson C P et al., Effects of selective phosphodiesterase inhibitors on polymorphonuclear leukocyte respiratory burst. J Allergy Clin Immunol 86: 801–808, 1990; Schade et al., The specific type III and IV phosphodiesterase inhibitor zardaverine suppresses formation of tumor necrosis factor by macrophages. European Journal of Pharmacology 230: 9–14, 1993).

1. Inhibition of PDE IV Activity

Methodology

The activity test was carried out according to the method of Bauer and Schwabe, which was adapted to microtiter plates (Naunyn-Schmiedeberg's Arch. Pharmacol. 311, 193–198, 1980). Here the PDE reaction takes place in the first step. In a second step, the 5'-nucleotide formed is cleaved to the uncharged nucleoside by a 5'-nucleotidase of the snake venom of *Ophiophagus hannah* (king cobra). In the third step, the nucleoside is separated from the remaining charged substrate on ion-exchange columns. The columns are eluted with 2 ml of 30 mM ammonium formate (pH 6.0) directly into minivials to which is additionally added 2 ml of scintillator fluid for counting.

The inhibitory values determined for the compounds according to the invention can be seen from the following Table A, from which the numbers of the compounds correspond to the numbers of the Examples.

TABLE A

Inhibition of PDE IV activity

| Compound | $-\log IC_{50}$ |
| --- | --- |
| 1 | 8.47 |
| 2 | 9.42 |
| 3 | 9.87 |
| 4 | 9.09 |
| 5 | 8.57 |
| 6 | 8.63 |
| 7 | 8.57 |
| 8 | 8.42 |

FORMULA SHEET I

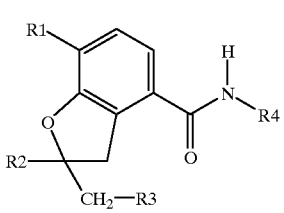
(I)

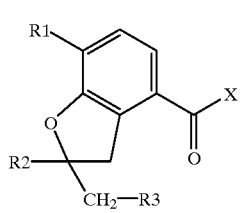
(II)

FORMULA SHEET II

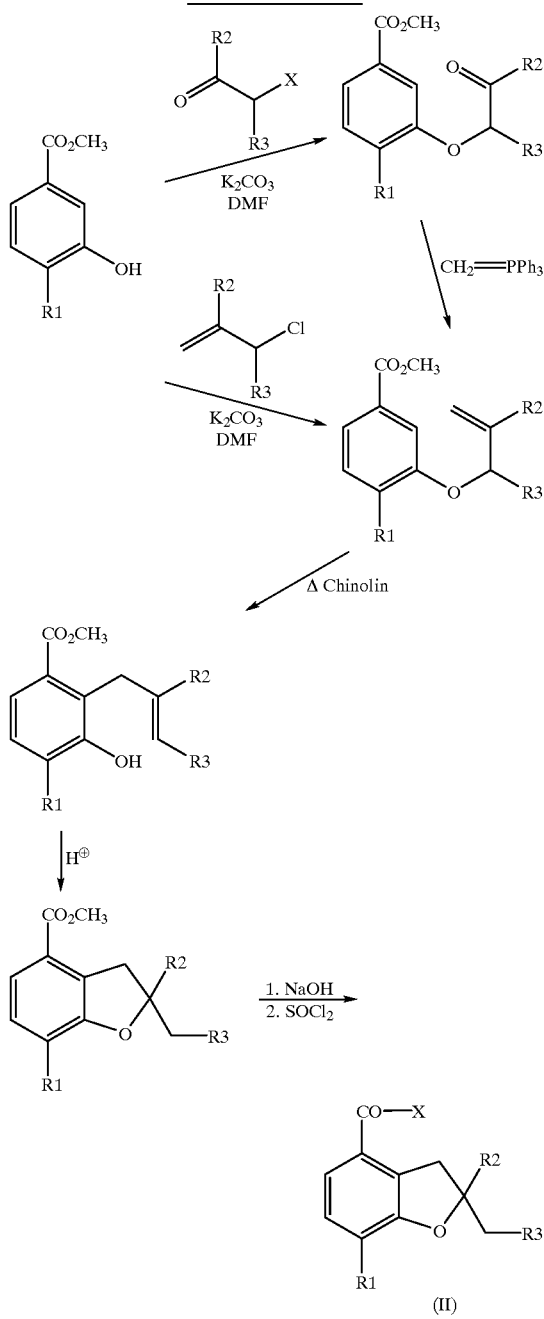

What is claimed is:

1. A compound of formula I

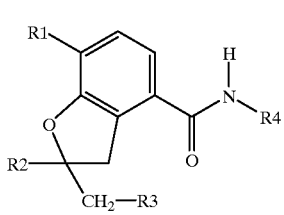
(I)

in which
R1 is 1–6C-alkoxy, 3–7C-cycloalkoxy, 3–7C-cycloalkylmethoxy, benzyloxy or completely or partially fluorine-substituted 1–4C-alkoxy,
R2 is 1–4C-alkyl and
R3 is hydrogen or 1–4C-alkyl, or
R2 and R3, together and including the two carbon atoms to which they are bonded, are a 5-, 6- or 7-membered hydrocarbon ring, optionally interrupted by an oxygen atom,
R4 is phenyl, pyridyl, R41-, R42- and R43-substituted phenyl or R44-, R45-, R46- and R47-substituted pyridyl,
R41 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino,
R42 is hydrogen, hydroxyl, halogen, amino, trifluoromethyl, 1–4C-alkyl or 1–4C-alkoxy,
R43 is hydrogen, halogen, 1–4C-alkyl or 1–4C-alkoxy,
R44 is hydroxyl, halogen, cyano, carboxyl, 1–4C-alkyl, 1–4C-alkoxy, 1–4C-alkoxycarbonyl or amino,
R45 is hydrogen, halogen, amino or 1–4C-alkyl,
R46 is hydrogen or halogen and
R47 is hydrogen or halogen,
a salt of the compound, an N-oxide of a pyridine wherein R4 comprises pyridyl or a salt of the N-oxide.

2. A compound of formula I as claimed in claim 1, in which
R1 is 1–4C-alkoxy, 3–5C-cycloalkoxy, 3–5C-cycloalkylmethoxy, or completely or partially fluorine-substituted 1–4C-alkoxy,
R2 is 1–4C-alkyl and
R3 is hydrogen or 1–4C-alkyl, or
R2 and R3, together and including the two carbon atoms to which they are bonded, are a cyclopentane, cyclohexane, tetrahydrofuran or tetrahydropyran ring,
R4 is phenyl, pyridyl, R41-, R42-, and R-43-substituted phenyl or R44-, R45-, R46- and R-47-substituted pyridyl,
R41 is halogen, cyno, carboxyl, 1–4C-alkyl, 1–4C-alkoxy, or 1–4C-alkoxycarbonyl,
R42 is hydrogen, halogen, 1–4C-alkyl or 1–4C-alkoxy,
R43 is hydrogen, halogen, 1–4C-alkyl or 1–4C-alkoxy,
R44 is halogen or 1–4C-alkyl,
R45 is hydrogen or halogen,
R46 is hydrogen or halogen and
R47 is hydrogen or halogen,
a salt of the compound, an N-oxide of a pyridine or a salt of the N-oxide.

3. A compound of formula I as claimed in claim 1 in which
R1 is 1–4C-alkoxy, 3–5C-cycloalkoxy, 3–5C-cycloalkylmethoxy, or completely or partially fluorine-substituted 1–4C-alkoxy,
R2 is 1–4C-alkyl and
R3 is hydrogen or 1–4C-alkyl, or
R2 and R3, together and including the two carbon atoms to which they are bonded, are a cyclopentane, cyclohexane, tetrahydrofuran or tetrahydropyran ring,
R4 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 3,5-difluoropyrid-4-yl, 2-chlorophenyl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
a salt of the compound, an N-oxide of a pyridine or a salt of the N-oxide.

4. A compound of formula I as claimed in claim 1 in which
R1 is methoxy, ethoxy, cyclopropylmethoxy, difluoromethoxy, trifluoromethoxy or 2,2,2-trifluoroethoxy,
R2 is methyl or ethyl and
R3 is hydrogen or methyl, or
R2 and R3, together and including the two carbon atoms to which they are bonded, are a cyclopentane, cyclohexane, tetrahydrofuran or tetrahydropyran ring,
R4 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 3,5-difluoropyrid-4-yl, 2-chlorophenyl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
a salt of the compound, an N-oxide of a pyridine or a salt of the N-oxide.

5. A compound of formula I as claimed in claim 1 in which
R1 is methoxy, ethoxy, cyclopropylmethoxy, difluoromethoxy, trifluoromethoxy or 2,2,2-trifluoroethoxy,
R2 is methyl or ethyl and
R3 i s hydrogen or methyl, or
R2 and R3, together and including the two carbon atoms to which they are bonded, are a cyclopentane, cyclohexane, tetrahydrofuran or tetrahydropyran ring,
R4 is 3,5-dichloropyrid-4-yl, 2,6-dichlorophenyl or 2,6-difluorophenyl,
a salt of the compound, an N-oxide of a pyridine or a salt of the N-oxide.

6. A process for the preparation of the compounds of the formula I as claimed in claim 1 and their salts, and also the N-oxides of the pyridines and their salts, which comprises reacting compounds of the formula II (see attached formula sheet I), in which R1, R2 and R3 have the meanings indicated in claim 1 and X is a suitable leaving group, with amines R4—NH$_2$, and, if desired, then converting compounds of the formula I obtained into their salts and/or converting pyridines obtained into the N-oxides and, if desired, then into the salts, or, if desired, then converting salts of the compounds of the formula I obtained into the free compounds.

7. A pharmaceutical composition comprising an effective amount of a compound according to claim 1 in combination with a pharmaceutically-acceptable excipient.

8. A method which comprises administering an effective amount of a compound according to claim 1 to a host afflicted with a condition amenable to such treatment.

9. A method according to claim 8 wherein the condition is an airway disorder.

10. A method according to claim 8 wherein the condition is a dermatosis.

11. In a method for compounding a medicament composition having an active ingredient for treating an airway disorder, the improvement wherein the active ingredient is a pharmaceutically-acceptable compound of claim 1.

12. In a method of compounding a pharmaceutical composition having an active ingredient for treating a dermatosis, the improvement wherein the active ingredient is a pharmaceutically-acceptable compound of claim 1.

* * * * *